United States Patent [19]

Selker

[11] Patent Number: 5,277,188

[45] Date of Patent: Jan. 11, 1994

[54] CLINICAL INFORMATION REPORTING SYSTEM

[75] Inventor: Harry P. Selker, Wellesley, Mass.

[73] Assignee: New England Medical Center Hospitals, Inc., Boston, Mass.

[21] Appl. No.: 721,157

[22] Filed: Jun. 26, 1991

[51] Int. Cl.[5] .......................................... A61B 5/0402
[52] U.S. Cl. ..................................... 128/696; 128/695
[58] Field of Search ................. 128/695–696, 702–705; 364/413.06

[56] References Cited

U.S. PATENT DOCUMENTS

| | | | |
|---|---|---|---|
| 4,315,309 | 2/1982 | Coli | 564/200 |
| 4,347,851 | 9/1982 | Jundanian | 128/668 |
| 4,610,254 | 9/1986 | Morgan et al. | 128/419 |
| 4,679,144 | 7/1987 | Cox et al. | 128/702 X |
| 4,893,270 | 1/1990 | Beck et al. | 364/900 |
| 4,945,477 | 7/1990 | Edwards | 364/413.06 |
| 4,957,115 | 9/1990 | Selker | 128/696 |
| 4,998,535 | 3/1991 | Selker et al. | 128/696 |
| 5,046,499 | 9/1991 | Berger | 128/695 X |

OTHER PUBLICATIONS

Michael W. Pozen, et al., "A predictive Instrument to Improve Coronary–Care Unit Admission Practices in Acute Ischemic Heart Disease", The New Englang Journal of Med., vol. 310 pp. 1273–1278, May 17, 1984.
Richard F. Gillum, M. D. et al., "International diagnostic criteria for acute myocardial infarction and acute stroke," American Heart Journal, p. 150 (Jul., 1984).

Primary Examiner—Lee S. Cohen
Assistant Examiner—Jeffrey R. Jastrzab
Attorney, Agent, or Firm—Fish & Richardson

[57] ABSTRACT

A clinical information reporting system for use with an electronic database for a health care facility, the electronic database containing records for a group of patients and operational information which is accessed and used during the course of operation of the facility, the records containing clinical information for said group of patients, the reporting system including an electrocardiograph which generates ECG-related data for the group of patients; database application logic for incorporating the ECG-related data for the group of patients into the database; and report generating logic for generating a process of care report from the information stored in the database, the process of care report presenting selected process of care information derived from the database as a function of a clinically meaningful class of the group of patients, wherein the clinically meaningful class is defined at least in part in terms of the ECG-related data supplied by the electrocardiograph and stored within the database.

15 Claims, 6 Drawing Sheets

FIG. 1

| Variable | Coefficient (bi) | | Value ($x_i$)* |
|---|---|---|---|
| CONSTANT ($b_o$) | -3.933 | | |
| CPAIN | 1.231 | Chest or left arm pain/pressure | 1 |
| | | Not present | 0 |
| SX1CPAIN | 0.882 | Chest or left arm pain chief complaint | 1 |
| | | Otherwise | 0 |
| MALESEX | 0.712 | Male | 1 |
| | | Female | 0 |
| AGE | -1.441 | Patient age 40 or less | 1 |
| | | Otherwise | 0 |
| AGE50 | 0.667 | Patient age greater than 50 | 1 |
| | | Otherwise | 0 |
| SEXAGE50 | -0.426 | Male patient age greater than 50 | 1 |
| | | Otherwise | 0 |
| QWAVE | 0.616 | ECG Q waves present | 1 |
| | | Otherwise | 0 |
| STEL | 0.314 | ECG S-T segment elevated 2mm or more | 2 |
| | | ECG S-T segment elevated 1-2mm | 1 |
| | | Otherwise | 0 |
| STDEP | 0.993 | ECG S-T segment depressed 2mm or more | 2 |
| | | ECG S-T segment depressed 1-2mm | 1 |
| | | ECG S-T segment depressed 0.5-1mm | 0.5 |
| | | Otherwise | 0 |
| TWEL | 0.095 | ECG T waves elevated ("hyperacute") | 1 |
| | | Otherwise | 0 |
| TWINV | 1.127 | ECG T-waves inverted 5mm or more | 2 |
| | | ECG T-waves inverted 1-5mm | 1 |
| | | ECG T-waves flat | 0.5 |
| | | Otherwise | 0 |
| TWISTDEP | -0.314 | <u>Both</u> STDEP and TWINV not 0 | 1 |
| | | Otherwise | 0 |

CLINICAL INFORMATION REPORTING SYSTEM

The U.S. Government has rights in this invention pursuant to Grant No. RO1HS05549 awarded by the National Institutes of Health.

BACKGROUND OF THE INVENTION

The invention relates to clinical information reporting systems.

Each year, over 500,000 Americans die of acute myocardial infarction (AMI, known as "heart attack"), including over 200,000 in hospitals. Were the medical advances of the last two decades consistently used, the mortality rate for hospitalized AMI patients would be much less. Medical care in this country's 6,000 hospitals varies, and current national AMI mortality rates are about twice those reported from major research centers. The problem is that physicians and hospitals do not consistently deliver optimal cardiac care.

Two fundamental problems underlie the failure to translate medical advances into results in this country's hospitals: 1) delays and errors in emergency room (ER) physician decision-making about the immediate care of the AMI patient, and 2) the lack of any credible and practical way to monitor and evaluate hospital AMI care results.

The key advances in AMI care relate to the very first hours of care: new medications and procedures for immediate use, and admission to the coronary care unit (CCU). Even short delays in treatment can cost lives in the first few hours, as can mistakes in CCU admission, but both are currently common. Delays occur as ER physicians try to sort out and treat AMI patients from among the many others they must evaluate. For example, the typical ER delay in giving thrombolytic therapy is about two hours, despite its well-known loss of its life-saving effect if not given promptly. Admission decisions to the CCU are also often suboptimal. of the early 1.5 million patients admitted to CCUs in this country each year, fewer than half have true acute cardiac ischemia (the diagnosis including AMI as well as "unstable angina pectoris", which can quickly progress to an AMI), thus filling CCUs with unnecessary admissions. More costly in lives, each year approximately 20,000 AMI patients are inadvertently sent home from the ER without any care.

Once primarily the concern of physicians and researchers, because of the scale of the problem, the Federal government is now looking for ways to monitor, evaluate and improve the delivery of AMI care. Over the past two years, separate expert panels have been convened by the Health Care Financing Administration (HCFA), the Agency for Health Care Policy and Research (AHCPR), the National Institutes of Health (NIH), and the Institute of Medicine of the National Academy of Science, to find ways to improve the delivery of cardiac services. In each case, these panels and agencies have concluded that two major approaches are needed: 1) in order to improve the quality and speed of physicians' emergency care of AMI patients, methods are needed to assist physicians' emergency decision-making; and 2) in order to detect suboptimal care and to encourage continuous improvement, methods are needed to objectively assess the quality of physicians' and hospitals' AMI care.

SUMMARY OF THE INVENTION

In general, in one aspect, the invention features a clinical information reporting system for use with an electronic database in a health care facility. The electronic database contains records for a group of patients and it contains operational information which is accessed and used during the course of operation of the facility. The patient records include clinical information for the group of patients. The reporting system includes an electrocardiograph which generates ECG-related data for the group of patients; database application logic for incorporating the ECG-related data for the group of patients into the database; and report generating logic for generating a process of care report from the information stored in the database. The process of care report presents selected process of care information derived from the database as a function of a clinically meaningful class of patients, wherein clinically meaningful class is defined at least in part in terms of the ECG-related data supplied by the electrocardiograph and stored within the database.

Preferred embodiments include the following features. Each of the patient records for a group of patients contains non-ECG related clinical information and the clinically meaningful class is defined in terms of the ECG-related data and non-ECG related clinical information stored within the database. The non-ECG related clinical information includes laboratory test results of blood enzyme analyses and the clinically meaningful class is defined in terms of the ECG-related data and the presence of an abnormal blood enzyme as indicated by the laboratory test results stored in the database. The abnormal blood enzyme is CPK. The database includes administrative information which is accessed and updated during the course of operation of the health care facility and the process of care information is derived at least in part from that administrative information. The database also includes patient billing information which is accessed and updated during the course of operation of the health care facility and the process of care information is derived at least in part from that patient billing information. The database contains triage decisions for the group of patients and the process of care report reports triage decisions for the clinically meaningful class of the group of patients.

In general, in another aspect, the invention features a clinical information reporting system including an electrocardiograph which generates ECG-related data for the group of patients; a predictive instrument which receives from the electrocardiograph ECG data for each patient of the group of patients and which computes a probability for each patient therefrom, the computed probability being a probability that patient is experiencing a cardiac problem; database application logic for incorporating the ECG-related data for the group of patients and the computed probability for each patient into the database; and report generating logic for generating a process of care report from the information stored in the database, the process of care report presenting selected process of care information derived from the database as a function of the computed probabilities supplied by the predictive instrument.

The invention gives the health care facility the ability to access and view operational, clinical and process of care information within its electronic databases in terms of meaningful clinical classes for cardiac patients. The availability of both patient ECG data and other clinical information (e.g., laboratory enzyme analysis for patients) within the same database enables the user of the database to sort and present information in terms of clinical classes that are defined on the basis of both ECG data and non-ECG data. Since the patient information can now be accessed in terms of meaningful clinical classes defined at least in part by the ECG data, the user can generate process of care reports that would be very useful for risk management, quality assurance, utilization review and physician feedback purposes. Thus, the invention enables the health care facility to much more effectively monitor and evaluate clinical care that is provided to cardiac patients.

Furthermore, such reports can be generated within the clinical setting and during the time frame in which they are needed (i.e., in real-time). The generation of such reports does not require the intervention of medical records clerks who must generate diagnostic codes for each patient based upon sometimes subjective and incomplete information supplied by the treating physician. Previously, if such reports had been desired, they could not be obtained in a timely manner but only through long, expensive research studies that required considerable manual effort and subjective or imprecise determinations of the diagnostic codes for the patients (i.e., the clinical class to which the patient belongs).

Also, in embodiments of the invention which incorporate a predictive instrument, the inclusion in the general database of the probability generated by the predictive instrument (e.g. the probability that acute ischemic heart disease is present) provides another useful and valuable variable for reporting and evaluating process of care information that can also be extracted from that database.

Other advantages and features will become apparent from the following description of the preferred embodiment and from the claims.

DESCRIPTION OF THE PREFERRED EMBODIMENT

STRUCTURE AND OPERATION

Figure 1:
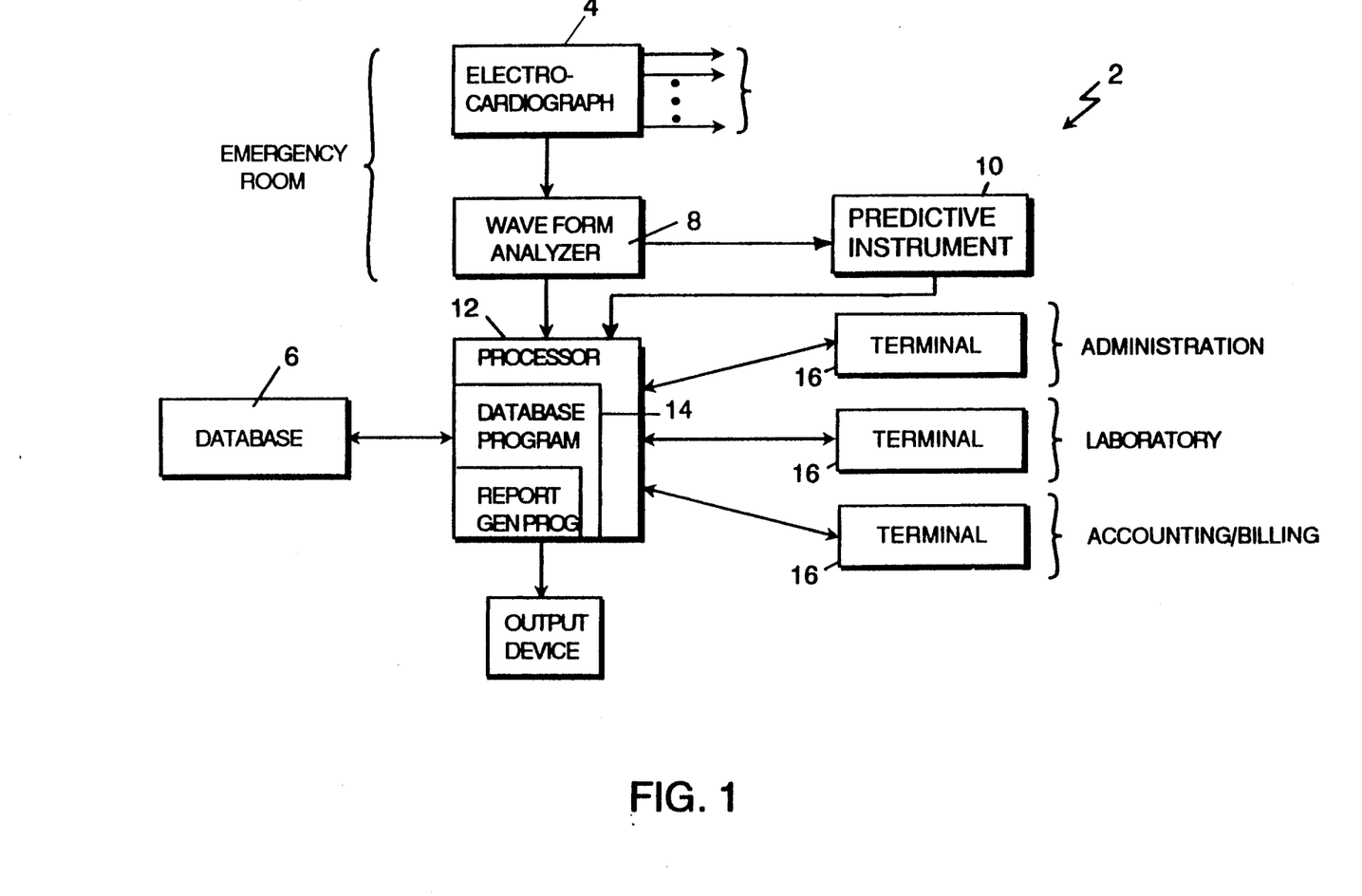
FIG. 1 is a block diagram of a clinical reporting system.

Referring to FIG. 1, in a clinical information reporting system 2, ECG-related data generated by an electrocardiograph 4 is incorporated into a database 6 which also contains other clinical information about patients seen at a health care facility, as well as operational information for the facility. Electrocardiograph 4 produces a digitized ECG waveform for the patient being monitored. The ECG waveform is processed by a waveform analyzer 8 which identifies and quantifies its important characteristics and features. Electrocardiograph 4 and waveform analyzer 8 may be part of a single instrument, for example, a Hewlett Packard Pagewriter XLi ®, which is a 80386-based self-interpreting electrocardiograph. The Pagewriter generates an output referred to as a "BLOB" (Binary Large OBject), which contains the digitized waveform as well as a measurement matrix containing the results of the waveform analysis.

The output of waveform analyzer 8 passes to a predictive instrument 10 which evaluates the condition of the patient and generates a probability that the patient is, for example, experiencing a particular type of cardiac condition. Predictive instrument 10 is designed in accordance with the design principles used for building other predictive devices such as the device for determining the probability of imminent death of the patient from cardiovascular disease such as is described in U.S. No. 4,957,115 to Dr. Harry P. Selker and the hand-held predictive instrument described by Michael W. Pozen et al. in "A Predictive Instrument to Improve Coronary-Care-Unit Admission Practices in Acute Ischemic Heart DiseaseI" The New England Journal of Medicine, Vol 310 pp. 1273-1278, May 17, 1984, both of which are incorporated herein by reference.

In the described embodiment, predictive instrument 10 is a TIPI (time-insensitive predictive instrument) which uses a logistic regression-based equation for computing the probability that the patient is experiencing acute cardiac ischemia. The logistic regression equation is of the form:

$$P = 100 \times [1 - 1/(1 + \exp(b_0 + \Sigma b_i x_i))],$$

where P is the probability of acute cardiac ischemia, $b_0$ is a constant, and the $b_i$'s are coefficients of the variables $x_i$ which are included in the model.

Figure 2:
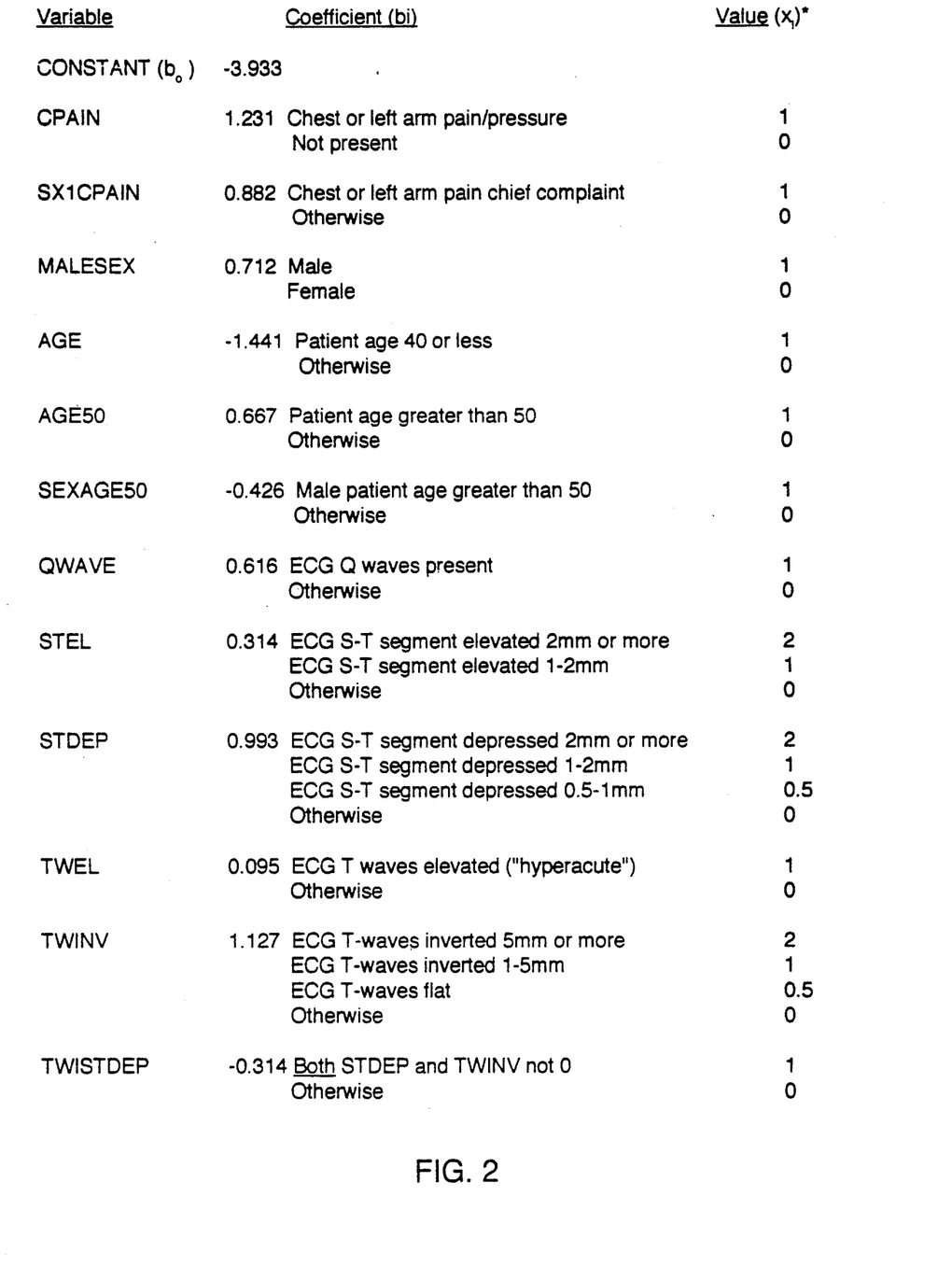
FIG. 2 presents the coefficients and variables of the logistic regression model used to compute the probability of acute cardiac ischemia.

The variables which are used in this equation are shown in FIG. 2 along with the values of the coefficients and the values which the $x_i$'s can take for the different variables. Note that only the largest x is used per variable. Also ECG findings must be present in at least two leads, and S-T segment and T wave changes are "normal" if secondary to right or left complete bundle branch blocks, left ventricular hypertrophy, or a paced QRS. Only one type of abnormality is coded each for S-T segment and for T wave per patient (exclusive of TWISTDEP), with elevation taking priority. Deviations are expressed in mm using the standard ECG scale of 1mm=0.1 mV.

The computer uses the inputs from electrocardiograph 4, waveform analyzer 8 to automatically compute the relevant probability using the above equation. The probability can be computed either in real time, while the patient is being evaluated, or it may be computed retrospectively.

The user performs the ECG in the usual way. At the time the ECG is being obtained, the user also enters patient identifying information and simple clinical data into the electrocardiograph. This includes, for example, patient date of birth, hospital ID#, age, sex, often a single diagnostic or symptomatic label (e.g. "chest pain", or "history of heart attack", etc.) medications, blood pressure, weight and perhaps other items which may be required by the computation that is to be performed by the predictive instrument.

The digitized ECG waveform, along with output from waveform analyzer 8, the computed probability from predictive instrument 10 and patient identifiers and other data which have been entered through electrocardiograph 4 by the physician are processed by a digital processor 12 which is running a database software program 14 such as, for example, the relational database program available from Sybase, Inc. and present in the Hewlett Packard ECG management system known as Tracemaster ®. Database software program 14 opens the appropriate file and adds the information to patient records stored to database 6. If database 6 contains a record for the relevant patient, database program 14 adds the ECG-derived information to the existing record for that patient. If database 6 does not yet include a record for the patient, database program 14 creates a new record for the patient, and stores the ECG-derived information in that new record.

Database 6 also contains non-ECG clinical information for patients including, for example, enzyme analysis, blood test results, urinalysis results, blood pressure readings, etc. which have been gathered during the evaluation and testing of the patients by the medical staff at the facility. Such non-ECG clinical information may be entered into database 6 in any of a number of different ways. For example, it may be automatically entered via a direct hook up with the laboratory assay machine which performs the test or it may be entered into database 6 through terminals 16 located elsewhere in the facility, such as, terminals found in the labs where the analysis is performed or terminals in the medical records department where medical records staff enter the handwritten notes generated by the medical staff who evaluate the patients Database 6 also stores a broad range of other information which is generated and accessed in the course of the daily operation of the health care facility. In other words, the ECG-derived data is integrated into database 6 with a larger collection of data relating to the patients treated at the health care facility, the medical staff which provide the health care, the resources available for administering the care and information relating to the operational aspects of the health care facility. For example, it contains patient billing information generated by the accounting and billing departments, administrative and personnel information including information about the resident training program and the experience of the medical staff within the residency program, and other information which is necessary to running the facility.

Electrocardiograph 4 provides patient data which enables the user to classify cardiac patients in a clinically meaningful way. meaningful clinical classes for cardiac patients may be defined in terms of diagnostic criteria which often require both ECG patient data as well as other clinical data (non-ECG data) for the patient. For example, the diagnostic criteria for determining whether a patient has experienced a nonfatal myocardial infarction includes diagnostic ECG and abnormal enzymes (e.g. creatine phosphokinase (CPK)). See, for example, Richard F. Gillum, M.D. et al., "International diagnostic criteria for acute myocardial infarction and acute stroke,"American Heart Journal, p. 150, (July, 1984), incorporated herein by reference, which presents diagnostic criteria for classifying cardiac patients. The stored ECG data available through the electrocardiograph is examined for the presence of the diagnostic ECG and laboratory results generated elsewhere in the cardiac care facility (and stored within the same database) are examined for the presence of the abnormal enzymes, which along with characteristic ECG findings (e.g. Q waves of greater than 40 msec duration) confirm and/or define the diagnosis of acute infarction.

Similarly, accurate identification of the patients who have experienced life-threatening hyperkalemic arrhythmic problems can be accomplished by examining patient ECG data along with other non-ECG data for the patient, namely, the patient's potassium level as determined by a test which is conducted by the laboratory, i.e., another department of the health care facility. Identification of members of the relevant diagnostic class need not depend upon the crude and often inaccurate diagnostic codes which are generated by medical records personnel who often are relied upon to enter patient medical information into a central database. Thus, by combining the ECG data with the general patient information database for the facility, i.e., the database which includes other clinical information for patients, the user has immediate access to all data which is necessary for making meaningful classifications of patients.

For cardiac patients, meaningful clinical classes may also be defined in terms of the ECG patient data combined with another category of non-ECG data such as the probability generated by the predictive instrument. With the electrocardiograph-generated data and the output of the predictive instrument incorporated into the general database for the facility, it becomes possible to easily generate a broad range of meaningful reports on the performance of the facility in providing cardiac care, i.e., reports based upon valid and meaningful clinical classifications of patients. Moreover, the presence of the ECG data and the output of the predictive instrument in the larger database containing nonECG data also makes it possible for the facility to generate those reports in real-time (i.e., while the patient is at the facility or within a short time after the report is requested by the user).

The electrocardiograph data within the database also enables the user to define an effective window into the data which is collected on patients that are diagnosed and/or treated by a health care facility. More specifically, it enables the user to produce reports about the process of care for cardiac patients which are based on meaningful clinical classes.

Moreover, since the electrocardiograph is a cardinal piece of equipment in the diagnosis and treatment of all patients passing through the facility that are suspected of having cardiac problems, it assures that the database is complete. That is, its use in the clinical information reporting system to create a patient record within the general database (or to add ECG data to an already existing patient record) for every potential cardiac patient assures that the underlying database includes all patients who had cardiac problems. Thus, any report generated from that database about cardiac care will more accurately reflect the actual care being provided by the facility. Since all patients who received an electrocardiograph are automatically added to the database, the user may be reasonably confident that the report does not exclude cardiac patients who have been treated by the facility but through oversight or error were not added to the database. For example, under current practice patients erroneously not admitted to the hospital have no in-patient records or data, and errors cannot be found for that population. Also since the user can sort and report operational and process of care data based upon ECG based criteria, the user has greater confidence in the accuracy of the identification of cardiac problem types. This is particularly important for generating reliable and accurate risk management, quality assurance and utilization review reports for the health care facility.

The report generating features available through the database software may be used to generate such reports. Since the ECG-related patient data is present within the general database, the database software can be used to sort and/or present patient data based on ECG-based diagnostic class criteria.

The reports of particular importance and which have not previously been available to the administrator of the health care facility, the health care insurer, to malpractice litigation risk management personnel or to hospital resource utilization review functions are those which relate to the process of care provided by the facility for clinical classes defined at least in part by ECG data. "Process of care" analysis is to be distinguished from "outcomell analysis, which looks at the results of the medical intervention, and from I'structurell analysis, which looks at the physical makeup, condition and quality of the health care facility. In general, "process of care" concerns the type and quality of the actual medical care which is provided to patients. The following list suggests several examples of measures of process of care:

Were patients with acute myocardial infarction admitted to the CCU?

Were patients with hyperkalemic arrhythmias appropriately treated with agents to lower their potassium level?

Do patients experiencing cardiac ischemia-related chest pain get nitroglycerine within five minutes of chest pain onset?

Are patients with cardiogenic shock given a Swan-Ganz catheter and appropriate medications?

Were patients triaged home from the ER of appropriately low likelihood (e.g. by the predictive instrument) of acute ischemia?

Process of care information may be derived from operational data stored within the database. The operational data might include, for example:

credentials and training information on the physicians and other members of the medical staff;

billing information which indicates the types of services that were provided to patients;

administrative information indicating such things as the length of stay;

data from real-time hospital operations;

data from pharmacy records;

triage location data;

billing information for the responsible MD;

lab data;

ICU nursing records; and orders for devices (e.g. Swan-Ganz catheters).

Examples of a variety of process of care reports that may be generated in real-time from the database are shown in FIGS. 3-6.

Figure 3:
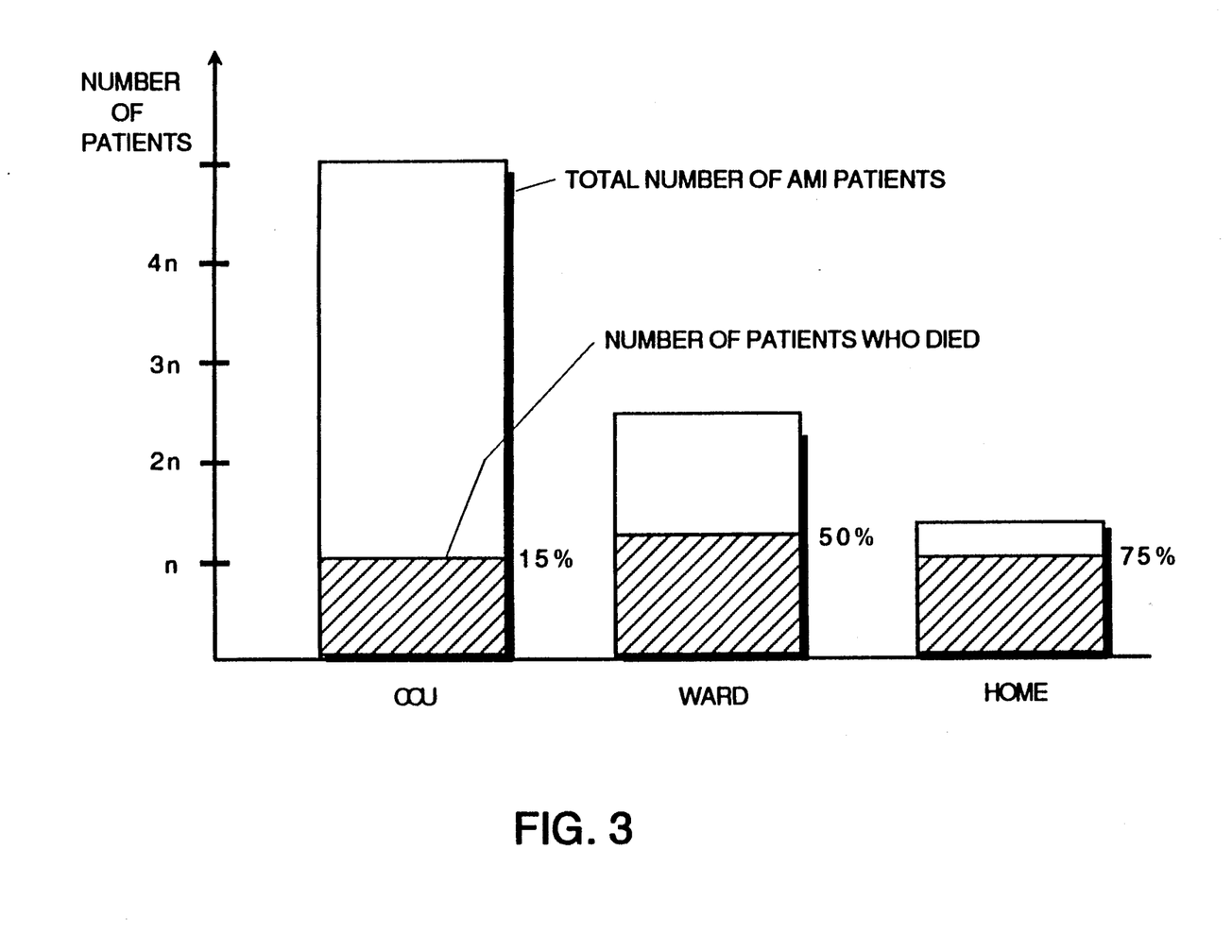
FIG. 3 is an example of a process of care report which may be generated from the database using ECG data to identify the relevant patient population (i.e., AMI patients)

FIG. 3 is a report of the total number of AMI patients who were sent to each triage location, i.e., CCU, ward or home, and the percentage of each group that died. The members of the relevant population (i.e., the members of the diagnostic class) are determined by ECG criteria (e.g. Q wave AMI) and CPK laboratory test results. The triage decision, i.e., where the AMI patient was sent is determined from billing and hospital information databases. Such a report is useful for quality assurance or risk management purposes in evaluating the correctness of the triage decisions that are being made.

Figure 4:
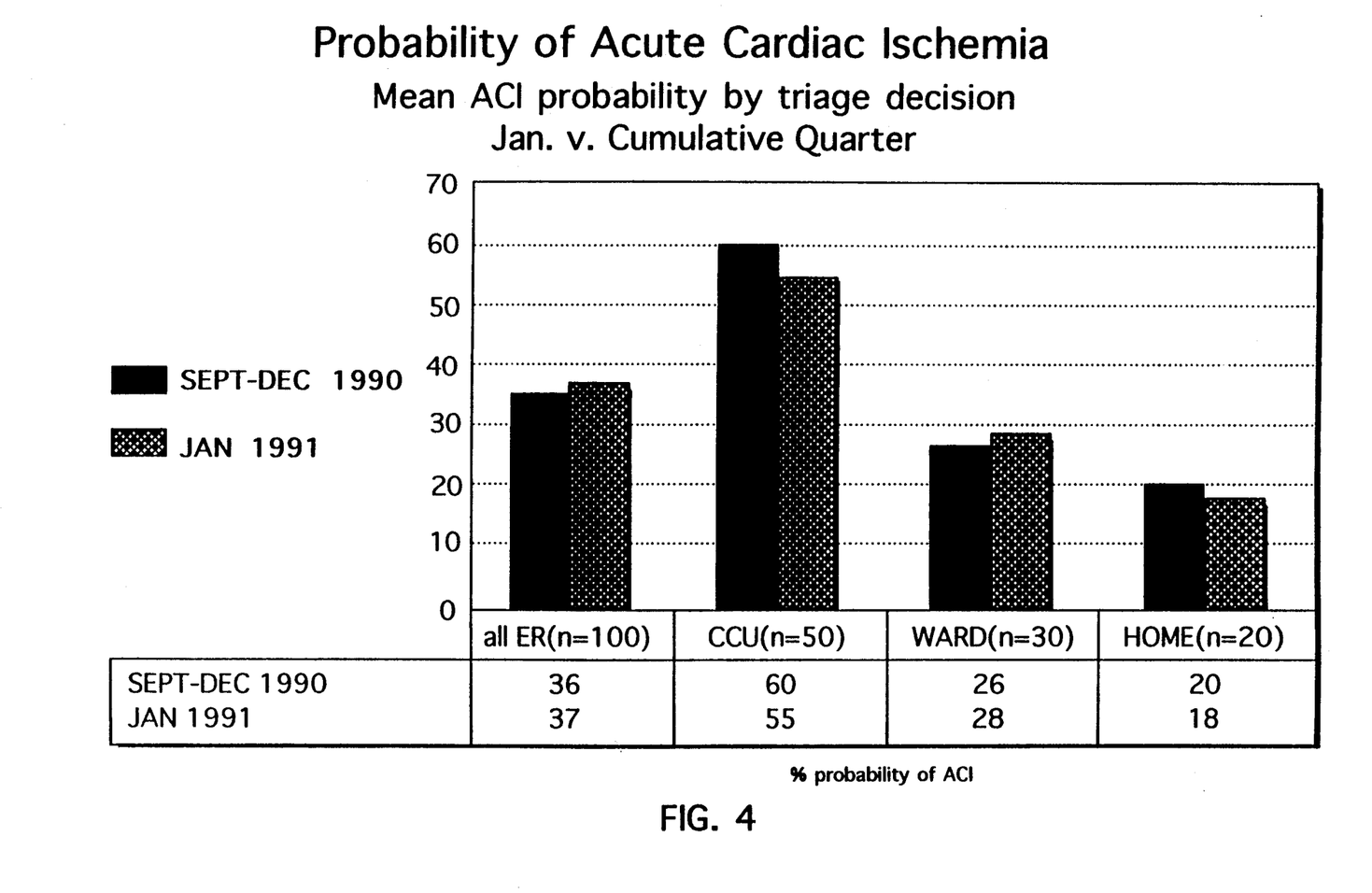
FIG. 4 is an example of another process of care report which may be generated from the database based upon predictive instrument generated ACI probabilities for the cardiac patients.

FIG. 4 is a report of the mean probability of acute cardiac ischemia (ACI) as a function of where people were sent (i.e., as a function of the triage decision) and as a function of time period. The leftmost set of bars presents the mean probability for all patients seen in the emergency room (ER). The next three sets of bars present the mean probability for patients sent to each of the three triage locations. In each set of bars the left bar reports the mean probability for the cumulative quarter from September 1990 through December 1990 and the right bar reports the statistics for January 1991. In this case, the predictive instrument which is used operates as described in the previously mentioned Pozen et al. reference. That is, the predictive instrument uses the ECG data for each patient to generate a probability that the patient was experiencing ACI.

The information reported in FIG. 4 is useful for risk management, utilization review, and quality assurance purposes, to name a few. For example, it helps assess who is being sent to the CCU and whether those patients really need CCU care. A low mean probability of ACI for the CCU patients would suggest that people are being sent to the CCU Who might more appropriately be handled by the ward or who even would be sent home.

Figure 5:
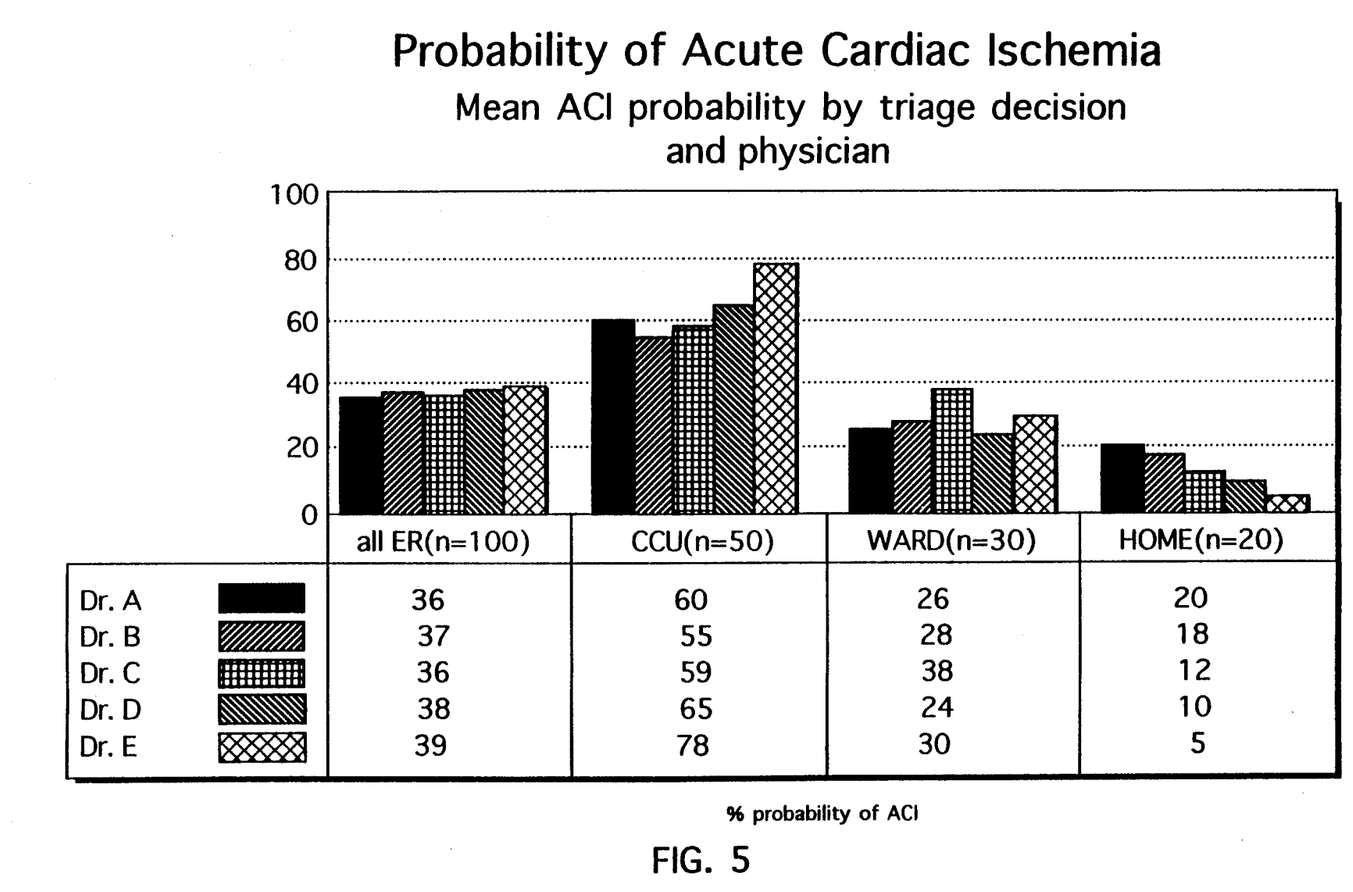
FIG. 5 is an example of a report of mean ACI probability by triage decision and by physician.

FIG. 5 is a report of the mean probability of ACI as a function of triage decision and as a function of the identity of the treating physician. The treating physicians are identified as Drs. A through E. Such a report is useful for determining another process of care concern, namely, is each of the doctors giving appropriate care. It could be used to identify those doctors, if any, who were improperly sending people with high ACI probabilities home and those doctors, if any, who were inappropriately using the limited CCU resources on patients with low ACI probabilities.

Figure 6:
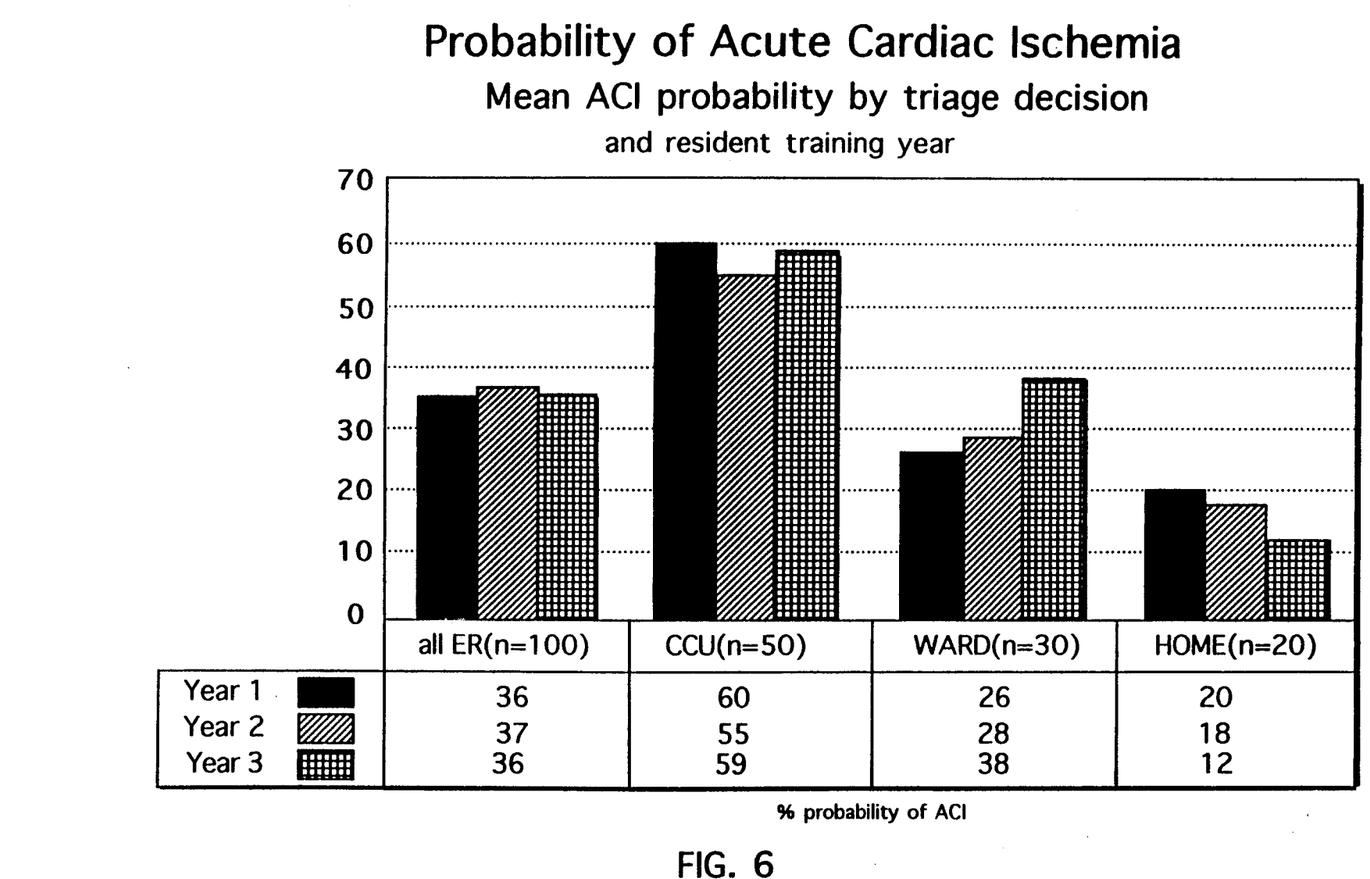
FIG. 6 is an example of a report of mean ACI probability by triage decision and by resident training year.

FIG. 6 is a report of the mean probability of ACI as a function of the triage decision and as a function of the residency training year of the treating resident physician. Such a report is useful for determining the effectiveness of the training of the resident physicians.

Other embodiments are within the following claims. For example, other monitoring devices (e.g. neonatal heart monitors) also play a correspondingly central role in diagnosing patient problems. Incorporating the output from such monitoring devices into the general operational database for the facility gives the user of the database a very valuable window through which to view all other patient related data in the database. That is, it enables the user to define meaningful clinical classes based in part on such monitoring data and to then generate in real-time process of care reports for such clinical classes of patients.

What is claimed is:

1. A clinical information reporting system for use with an electronic database for a health care facility, said electronic database containing records for a group of patients, there being at least one record for each patient of said group of patients, said database also containing operational information which is accessed and used during the course of operation of the facility, said records containing clinical information for said group of patients, said reporting system comprising:

an electrocardiograph means for generating ECG-related data for reach of the patients of the group of patients;

a database application means for incorporating the ECG-related data for said group of patients into the records for the patients of said group of patients; and a report generating means for generating a process of care report from the information stored in said database, said process of care report presenting selected process of care information derived form said database as a function of a clinically meaningful class of said group of patients, wherein said clinically meaningful class is defined at least in part in terms of the ECG-related data supplies by said electrocardiograph means and stored within said database.

2. The clinical information reporting system of claim 1 wherein each of said patient records for a group of patients contains non-ECG related clinical information and wherein said clinically meaningful class is defined in terms of the ECG-related data supplied by said electrocardiograph means and stored within said database and non-ECG related clinical information sorted within said database.

3. The clinical information reporting system of claim 2 wherein said non-ECG related clinical information includes laboratory test results of blood enzyme analyses and wherein said clinically meaningful class is defined in terms of the ECG-related data supplied by said electrocardiograph means and stored within said database and the presence of an abnormal blood enzyme as indicated by said laboratory test results stored in said database.

4. The clinical information reporting system of claim 3 wherein said abnormal blood enzyme is CPK.

5. The clinical information reporting system of claim 1 wherein said database includes administrative information which is accessed and updated during the course of operation of the health care facility and wherein said process of care information is derived at least in part from said administrative information.

6. The clinical information reporting system of claim 1 wherein said database includes patient billing information which is accessed and updated during the course of operation of the health care facility and wherein said process of care information is derived at least in part from said patient billing information.

7. The clinical information reporting system of claim 1 wherein said database contains triage decisions for said group of patients and wherein said process of care report reports triage decisions for said clinically meaningful class of said group of patients.

8. A clinical ion reporting system for use with an electronic database for health care facility, said electronic database containing records for a group of patients, there being at lest one record for each patient of said group of patients, said database also containing operationl information which is accessed and used during the course of operation of the facility, said records containing clinical information for said group of patients, said reporting system comprising:

an electrocardiograph mans for generating ECG-related data for each of the patients of the group of patients;

a predictive instrument means or receiving from said electrocardiograph means ECG data for each patient of said group of patients and computing a probability for each patient therefrom, said computed probability for each patient being a probability that patient is experiencing a cardiac problem;

a database application means for incorporating said ECG-related data for said group of patients and the computed probability for each patient into the records for the patients of said group of patients; and a report generating means for generating a process of care report from the information stored in said database, said process of care report presenting selected process of care information derived from said database as a function of the computed probabilities supplied by said predictive instrument means.

9. The clinical information reporting system of claim 8 wherein each of said patient records for the group of patients contains non-ECG related clinical information and wherein said clinically meaningful class is defined in terms of the ECG-related data supplied by said electrocardiograph means and stored within said database and non-ECG related clinical information stored within said database.

10. The clinical information reporting system of claim 9 wherein said non-ECG related clinical information includes laboratory test results of blood enzyme analyses and wherein said clinically meaningful class is defined in terms of the ECG-related data supplied by said electrocardiograph means and stored within said database and the presence of an abnormal blood enzyme as indicted by said laboratory test results stored in said database.

11. The clinical information reporting system of claim 10 wherein said abnormal blood enzyme is CPK.

12. The clinical information reporting system of claim 8 wherein said database includes administrative information which is accessed and updated during the course of operation of the health care facility and wherein said process of care information is derived at least in part from said administrative information.

13. The clinical information reporting system of claim 8 wherein said database includes patient billing information which is accessed and updated during the course of operation of the health care facility and wherein said process of care information is derived at lest in part from said patient billing information.

14. The clinical information reporting system of claim 8 wherein said database contains triage decisions for said group of patients and wherein said process of care report reports triage decisions or said clinically meaningful class of said group of patients.

15. A method of reporting clinical information about a group of patients in a health care facility, said method comprising:

storing records for the group of patients in an electronic database, there being a record for each patient of said group of patients, each of said records containing clinical information for a corresponding patient of said group of patients;

storing operational information for said facility in said electronic database, said operational information relating to operation of the facility;

generating ECG-related data for each of the patients of the group of patients;

incorporating the ECG-related data for said group of patients into the records for the patients of said group of patients; and generating a process of care report from the information stored in aid database, said process of care report presenting selected process of care information derived from said database as a function of a clinically meaningful class of said group of patients, wherein said clinically meaningful class is defined at least in part in terms of the ECG-related data stored within said database.

* * * * *

UNITED STATES PATENT AND TRADEMARK OFFICE
CERTIFICATE OF CORRECTION

PATENT NO. : 5,277,188

DATED : January 11, 1994

INVENTOR(S) : Harry P. Selker

It is certified that error appears in the above-identified patent and that said Letters Patent is hereby corrected as shown below:

On title page, item [56] "OTHER PUBLICATIONS", column 2, line 1, replace "Englang" with --England--;

Column 1, line 40, replace "suboptimal.of the early" with --suboptimal. Of the early--;

Column 6, line 34, replace "nonECG" with --non-ECG--;

Column 7, line 20, replace "outcomell analysis" with --outcome analysis--;

Column 7, line 21, replace "I'structurell" with --structure--;

Column 9, claim 1, line 11, replace "form" with --form--;

Column 9, claim 8, line 54, replace "ion" with --information--;

Column 9, claim 8, line 66, replace "means or" with --means for--;

UNITED STATES PATENT AND TRADEMARK OFFICE
CERTIFICATE OF CORRECTION

PATENT NO. : 5,277,188
DATED : January 11, 1994
INVENTOR(S) : Harry P. Selker

It is certified that error appears in the above-indentified patent and that said Letters Patent is hereby corrected as shown below:

Column 10, claim 13, line 46, replace "at lest" with --at least--.

Signed and Sealed this

Fifth Day of July, 1994

Attest:

BRUCE LEHMAN

Attesting Officer          Commissioner of Patents and Trademarks